United States Patent [19]

Euser

[11] Plant 4,100

[45] Sept. 6, 1977

[54] CARNATION PLANT NAMED APACHE

[75] Inventor: Anthony Euser, Broomfield, Colo.

[73] Assignee: Denver Wholesale Florists Company, Denver, Colo.

[21] Appl. No.: 731,833

[22] Filed: Oct. 12, 1976

[51] Int. Cl.[2] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new variety of carnation plant of the American type, particularly adapted to greenhouse culture for cut flower production and distinguished by the variegated purple-on-white coloring of its blossoms and its profuse and continuous spray-type production of flowers from early Spring through Fall on sturdy, upright and vigorous plants.

1 Drawing Figure

BACKGROUND OF THE NEW PLANT

This new carnation plant originated in my greenhouse at Bloomfield, Colo., as the sport of White Elegance (unpatented) and was discovered by me on Apr. 6, 1973. The very unusual coloring of this flower prompted me to reproduce it by means of cuttings and the resulting plants have since been propagated, by cuttings, through several successive generations at Bloomfield, Colo., and at Denver, Colo., during the course of which its novel characteristics have been observed to hold true from generation to generation and appear to be firmly fixed. Propagation of this new carnation variety is now being done on a commercial scale at Denver, Colo.

DESCRIPTION OF THE DRAWINGS

My new variety of carnation plant is illustrated by the accompanying photographic drawing which, in full color, shows a bud about to open, a bud with petals beginning to unfurl, and several stages of the opened flower, the color rendition being as nearly true as it is reasonably possible to obtain by conventional photographic procedures.

DESCRIPTION OF THE NEW PLANT

The following is a detailed description of my new variety of carnation plant based upon observations of greenhouse grown plants made at Denver, Colo., in the Summer of 1976, the color designations being according to the Dictionary of Color by Maerz & Paul, 2nd Edition, McGraw-Hill 1950.

THE PLANT

Origin: Sport.
Parentage: White Elegance (unpatented).
Classification:
*Botanic.—Dianthus caryophyllus.*
*Commercial.*—Greenhouse carnation for cut flowers.
Form: Bush.
Height: About 90 cm.
Growth: Sturdy and upright.
*Growth rate.*—16 weeks to flowering.
*Stem size.*—40 cm. long, 2.3 cm. circumference.
Branching: Normal, with 4 to 6 branches on the principal stem.
Foliage: Quantity — Abundant, more than 100 leaves.
*Leaf size.*—Medium to small.

*Leaf shape.*—Lanceolate with acuminate apex and entire margin.
*Texture.*—Smooth.
*Ribs and veins.*—Prominent mid-rib.
*Color.*—Upper side — Blueish-green. Under side — Green.
*Petiole.*—None. The leaf is amplexicaul.

THE BUD

Size: Small. Diameter about 13 mm. Length about 23 mm.
Form: Oval-shaped, but pointed at tip end.
Opening rate: 24 to 48 hours.
Color:
*When sepals first divide.*—White with purple marks.
*When petals begin to unfurl.*—Variegated-purple on white.
Sepals: Hooded over bud until dividing.
*Shape.*—Generally oval with acuminate tip.
*Condition after blooming.*—Upstanding. Tips do not curl back.
*Color.*—Inside — Whitish-green. Outside — Light green.
Calyx: Form — Funnel-shaped.
*Aspect.*—Smooth.
*Splitting.*—Calyx does not split.
Peduncle: Rigid and erect.
*Color.*—Blueish-green.

THE FLOWER

Blooming habit: Profuse and continuous, Spring through Fall.
Size of bloom: Small. Diameter — 50 mm. Depth — 42 mm.
Borne: As a spray-type of inflorescence.
Shape: Flat. Form does not change.
Petalage: Number of petals — About 45.
*Arrangement.*—Alternate whorls.
*Form.*—Fan shaped with fluted or ruffled ends and serrated margins.
*Texture.*—Soft.
*Appearance.*—Satiny.
*Color.*—Upper and reverse sides of all petals — Randomly splotched purple (Plate 6 — H6 to I6) on white background.
Petaloids: None.
Peduncle: Normal for spray-type carnations.

*Length.*—12 to 15 cm., varying from bloom to bloom.

Fragrance: None.

Persistence: Flowers hang on and dry.

Lasting Quality:

*On plant.*—5 to 6 days.

*As a cut flower.*—12 to 14 days.

REPRODUCTIVE ORGANS

Stamens:

*Anthers.*—5 in number.

*Arrangement.*—Circular around pistil.

*Filaments.*—25 mm. long. Color: White.

Pollen: Color — Greyish-white.

Pistils: Number — 3.

*Styles.*—18 mm. long.

*Stigmas.*—Color — White; purple tipped.

Ovaries: One per pistil.

My new variety of carnation plant is particularly distinguished by the very unusual coloration of its blossoms which with the very random purple on white markings of the individual petals present a very attractive burst of color. The variety closest to this new plant is Purple Haze (unpatented). However, this new plant has flowers of a more reddish-purple color and instead of lines or streaks, as in Purple Haze, has random splotches of color with no two petals being exactly the same in pattern or amount. The overall effect, however, is quite uniform — flower to flower.

I claim:

1. A new and distinct variety of carnation plant, substantially as herein shown and described, characterized by the randomly variegated purple on white coloration of its flowers, and by the profuse production of spray-type blooms on strong upright stems.

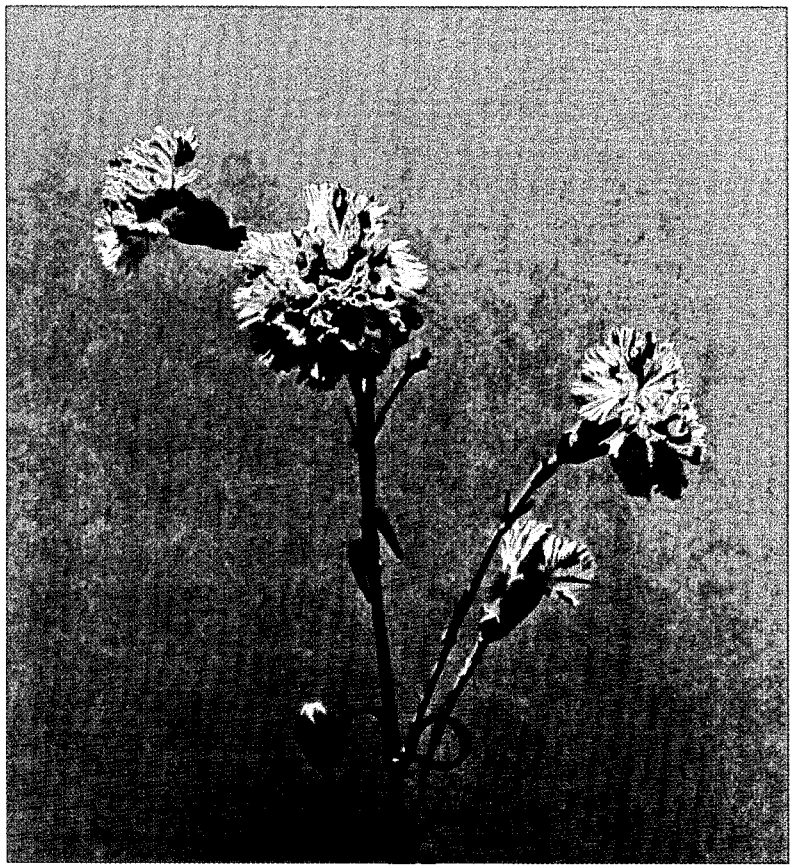

* * * * *